(12) United States Patent
Campbell et al.

(10) Patent No.: US 12,286,612 B2
(45) Date of Patent: Apr. 29, 2025

(54) CONTAINERS CONTAINING DEGRADABLE CARRIERS

(71) Applicant: SAINT-GOBAIN PERFORMANCE PLASTICS CORPORATION, Solon, OH (US)

(72) Inventors: Katie Campbell, Northborough, MA (US); Natasha Anna Boghosian, Boston, MA (US); Natalie Fekete, Marlborough, MA (US); Rachel Z. Pytel, Newton, MA (US)

(73) Assignee: Saint-Gobain Performance Plastics Corporation, Solon, OH (US)

( * ) Notice: Subject to any disclaimer, the term of this patent is extended or adjusted under 35 U.S.C. 154(b) by 893 days.

(21) Appl. No.: 16/730,660

(22) Filed: Dec. 30, 2019

(65) Prior Publication Data
US 2020/0209233 A1    Jul. 2, 2020

Related U.S. Application Data

(60) Provisional application No. 62/786,913, filed on Dec. 31, 2018.

(51) Int. Cl.
*C12M 1/00* (2006.01)
(52) U.S. Cl.
CPC .................. *C12M 23/14* (2013.01)
(58) Field of Classification Search
CPC ........... C12M 23/14; B01L 3/50; B01L 3/505; G01N 33/54386; G01N 33/545; G01N 33/547; C12N 5/06; C12N 5/0018; C12N 5/0068; C12N 5/0075; C12N 11/02; C12N 11/10; C12N 11/12; C12N 11/08; C12N 11/06; C12N 2531/00; C12N 2533/00; C12N 2533/70; C12N 2533/20;
(Continued)

(56) References Cited

U.S. PATENT DOCUMENTS

| 6,126,835 A | 10/2000 | Berbera-Guillem |
| 2005/0026230 A1 | 2/2005 | Matsumura |

(Continued)

FOREIGN PATENT DOCUMENTS

| WO | 2011097420 A2 | 8/2011 | |
| WO | WO2017169259 A1 * | 10/2017 | ............ C12M 23/20 |

OTHER PUBLICATIONS

Ding et al. ("Recent advances of PLGA micro/nanoparticles for the delivery of biomacromolecular therapeutics" Materials Science & Engineering C 92 (2018) 1041-1060 (Year: 2018).*

(Continued)

*Primary Examiner* — Christopher L Chin
(74) *Attorney, Agent, or Firm* — McDonnell Boehnen & Hulbert & Berghoff LLP

(57) ABSTRACT

This disclosure relates to containers (e.g., in the form of bags) comprising a fluoropolymer and containing a degradable carrier comprising biological agent-capturing moieties, to cell isolation systems comprising such containers, and to methods for cultivating a biological agent using such containers. In one embodiment, the disclosure provides a container having an outer surface and an inner surface, the inner surface comprising a fluoropolymer, and contained in the container, a degradable carrier; wherein the carrier comprises a plurality of biological agent-capturing moieties.

25 Claims, 3 Drawing Sheets

(58) Field of Classification Search
CPC ............ C12N 2533/72; C12N 2533/74; C12N 2533/76; C12N 2533/78; C12N 2539/00; C12N 2539/10
USPC ........ 435/372.3, 34, 39, 176, 177, 178, 179, 435/180, 181, 373, 374, 383, 395, 396, 435/397, 402, 403; 422/555
See application file for complete search history.

(56) References Cited

U.S. PATENT DOCUMENTS

| | | |
|---|---|---|
| 2005/0196828 A1 | 9/2005 | Zheng |
| 2006/0178491 A1 | 6/2006 | Tanaka |
| 2006/0254963 A1 | 11/2006 | Kanamori |
| 2010/0317112 A1 | 12/2010 | Yang |
| 2011/0027889 A1 | 2/2011 | McCarthy |
| 2012/0264117 A1 | 10/2012 | Sanders |
| 2014/0287512 A1 | 9/2014 | Kaisermayer |
| 2016/0061840 A1 | 3/2016 | Lee |
| 2016/0178490 A1 | 6/2016 | Civel |
| 2016/0178491 A1* | 6/2016 | Civel ............... G01N 33/54393 427/230 |
| 2016/0367481 A1* | 12/2016 | Zale ...................... A61K 47/34 |
| 2017/0283758 A1* | 10/2017 | Totani .................... C07K 17/08 |
| 2019/0264159 A1 | 8/2019 | Matsumoto |

OTHER PUBLICATIONS

International Search Report and Written Opinion in PCT/US2019/068983, dated May 1, 2020.

K.-T. Guo et al., "A New Technique for the Isolation and Surface Immobilization of Mesenchymal Stem Cells from Whole Bone Marrow Using High-Specific DNA Aptamers," Stem Cells, 24, 2220-2231 (2006).

J.K. Herr et al., "Aptamer-Conjugated Nanoparticles for Selective Collection and Detection of Cancer Cells," Anal. Chem., 78, 2918-2924 (2006).

Y. Pan et al., "Selective collection and detection of leukemia cells on a magnet-quartz crystal microbalance system using aptamer-conjugated magnetic beads," Biosensors and Bioelectronics, 25, 1609-1614 (2010).

D. Pappas & K. Wang, "Cellular separations: a review of new challenges in analytical chemistry," Analytical Chimica Acta, 601, 26-35 (2007).

* cited by examiner

CONTAINERS CONTAINING DEGRADABLE CARRIERS

CROSS-REFERENCE TO RELATED APPLICATIONS

This application claims the benefit of priority of U.S. Provisional Patent Application No. 62/786,913, filed Dec. 31, 2018, which is hereby incorporated herein by reference in its entirety.

BACKGROUND OF THE DISCLOSURE

Field of the Disclosure

This disclosure relates generally to containers (such as bags) containing degradable carriers. More particularly, the present disclosure relates to containers such as bags comprising a fluoropolymer and containing a degradable carrier comprising biological agent-capturing moieties, to cell isolation systems comprising such bags, and to methods for cultivating a biological agent using such bags.

Technical Background

Cell culture and cell isolation are important processes in a number of applications. For example, certain cells for use in therapeutic applications (e.g., immunotherapy, regenerative medicine, etc.) are typically isolated and cultured in vitro. For example, cells such as progenitor cells and mesenchymal stem cells, and monocytes and other immune cells are present in blood in relatively low concentrations, and accordingly are typically isolated from blood and cultured in vitro. Similarly, neuronal cells, cardiomyocytes, epithelial cells, and other cells for regenerative medicine (e.g., bone repair, skin repair, pancreatic islets regeneration, etc.) can be cultured in vitro.

Fluoropolymer bags are commonly used for cell cultures. Such bags are typically inexpensive, disposable, portable and easy to use. Conventionally, cells and feed medium are mixed within the culture bag. As nutrients are consumed and cell waste accumulates, the feed medium must be removed and replenished. Because cells can remain suspended within the bag, the desired cells can be removed along with the depleted medium.

One conventional cell isolation process involves selectively anchoring a desired cell to a solid support. For example, T cells, which play a central role in cell-mediumted immunity, can be distinguished from other lymphocytes by the presence of a T cell receptor (TCR) on the cell surface. A solid support having attached proteins capable of binding T cell receptors will selectively capture T cells within a cell culture, while undesired cells remain suspended. However, releasing captured cells, for example, by cleaving the anchoring protein, can undesirably alter the isolated cells.

Accordingly, there remains a need for cell culture and isolation articles that facilitate improved retention of desired cells.

SUMMARY OF THE DISCLOSURE

In one aspect, the disclosure provides a container (e.g., in the form of a bag) having an outer surface and an inner surface, the inner surface comprising a fluoropolymer, and contained in the container, a degradable carrier; wherein the carrier comprises a plurality of biological agent-capturing moieties.

In another aspect, the disclosure provides a method for cultivating a biological agent, comprising providing a container as described herein, the container containing the biological agent; mixing the biological agent and the carrier in a first aqueous medium contained in the container; removing first aqueous medium from the container; adding a second aqueous medium to the container; and degrading the carrier.

Other aspects of the disclosure will be apparent to the person of ordinary skill in the art in view of the disclosure herein.

DETAILED DESCRIPTION

The disclosure relates to containers (e.g., bags) having an inner surface comprising a fluoropolymer and containing a degradable carrier comprising biological agent-capturing moieties. The disclosure demonstrates that desired cells can be captured and physically separated from a suspension within the container, and can further be resuspended without deleteriously affecting cell function by degrading the carrier.

The containers of the disclosure can be provided in a number of forms. One especially convenient form is a bag, e.g., formed from one or more sheets of fluoropolymeric material as described herein. The person of ordinary skill in the art will be familiar with bag structures such as those used in cell culture, and will be able to adapt conventional bag structures for use in bags and methods of the disclosure based on the description herein Of course, the person of ordinary skill in the art will appreciate that the containers of the disclosure can be provided in a number of other forms, e.g., flasks, tubes, dishes.

Figure 1:
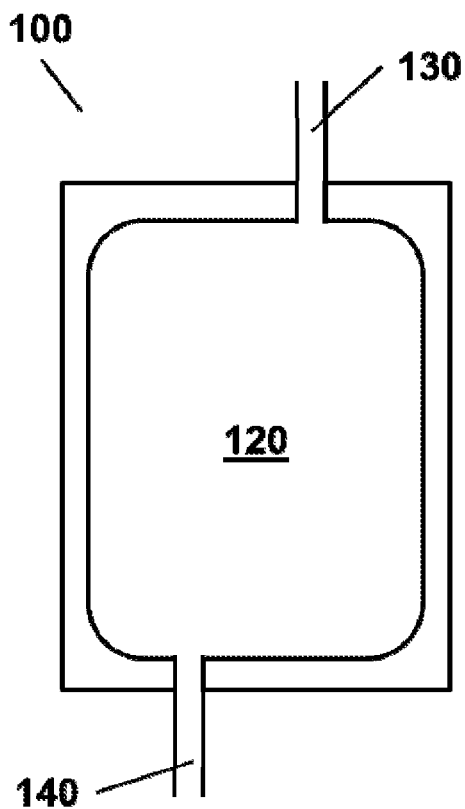
FIG. 1 is a schematic top-down (top) and cross-sectional (bottom) view of a bag according to one embodiment of the disclosure.
Figure 1:
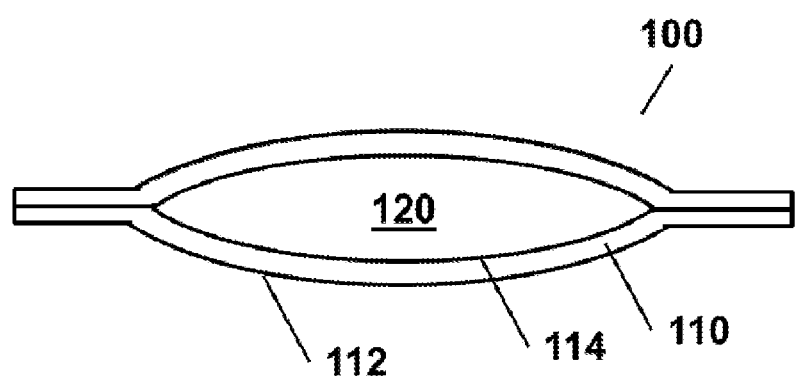

Accordingly, one aspect of the disclosure is a container, e.g., in the form of a bag having an outer surface and an inner surface, the inner surface comprising a fluoropolymer. An embodiment of such a bag is shown in schematic top-down view (top) and cross-sectional view (bottom) in FIG. 1. Bag 100 of FIG. 1 includes a bag wall 110 having an outer surface 112 and an inner surface 114, and further includes ports 130 and 140, located at opposite ends of the bag for adding or removing medium (e.g., feed medium or waste medium, respectively) to or from the bag. The person of ordinary skill in the art will appreciate that the number and location of ports are not particularly limited, and accordingly can be positioned, for example, for convenience of use or manufacture. Bag 100 can be the product of bonding two fluoropolymer-containing sheets (e.g., two sheets having a layer of fluorinated ethylene propylene sheets on an inside surface thereof) together at their edges (e.g., by laser welding, corona discharge, radiation, heat or melt lamination, etching, plasma treatment, wetting, adhesives, or combinations thereof) to form compartment 120. Ports 130 and 140 can be sealable to provide a sealed compartment 120.

The container wall can be uniform in its composition, or alternatively can include two or more distinct domains (e.g., two or more layers). For example, bonding two fluoropolymer sheets together, then coating the bonded sheets can provide an outer surface 112 differing in composition from inner surface 114. Similarly, bonding two multi-layer sheets together can provide an outer surface 112 differing in composition from inner surface 114. Multilayer sheets can be formed of both fluorpolymeric and nonfluorinated polymer materials; in such cases, a fluoropolymer layer can be provided at the inner surfaces of one or more of the multi-layer sheets. The thickness of the container, the volume of the compartment, and the shape of the container and/or compartment are not particularly limited, and can be selected for convenience of use or manufacture, and/or to suit a specific application. For example, the thickness of the container wall can be within the range of 0.0003 inches to 0.2 inches, and the volume of the compartment can be within the range of 100 mL to 100 L.

Figure 2:
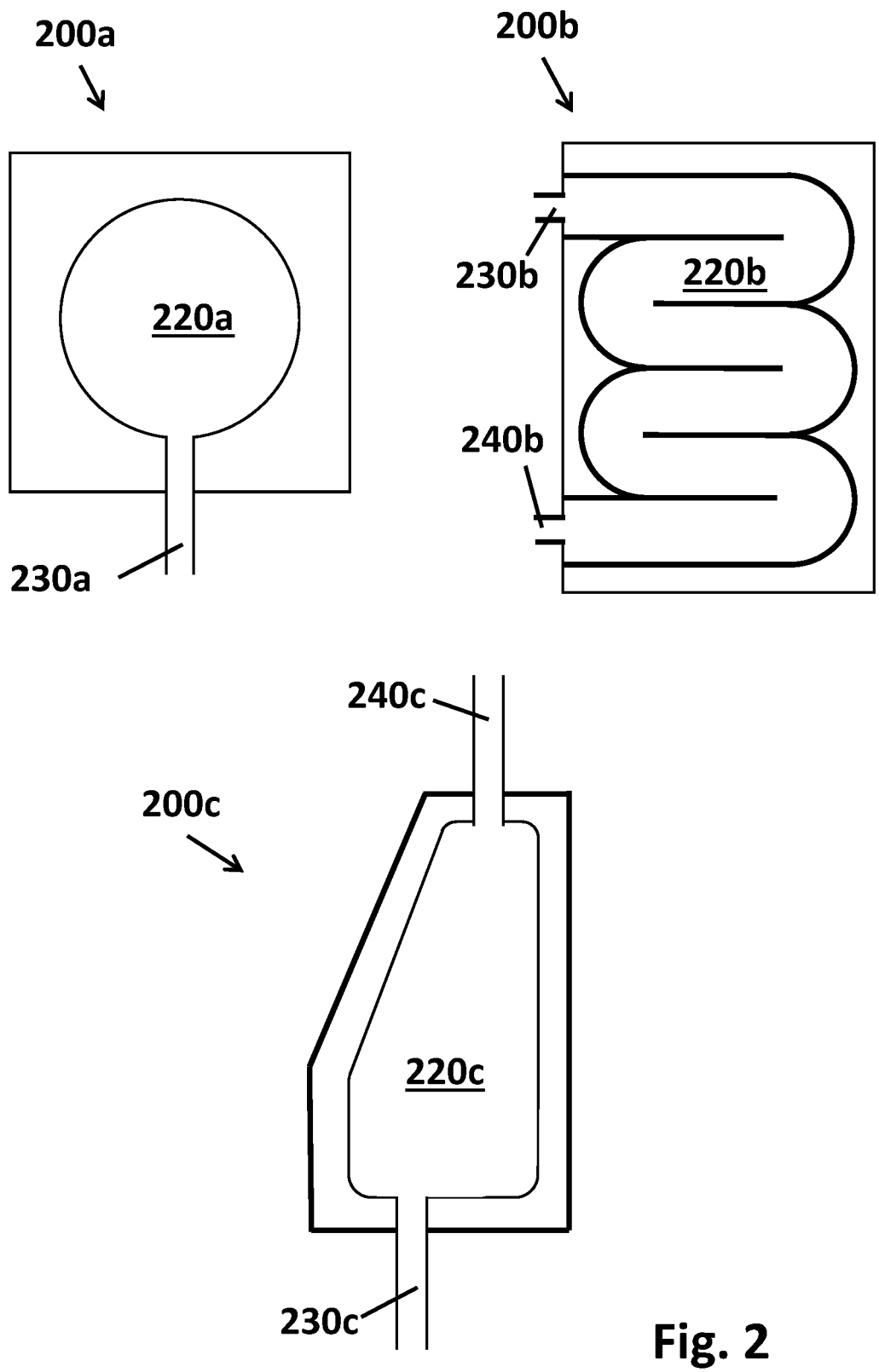
FIG. 2 is a schematic top-down view of bags according to certain embodiments of the disclosure.

FIG. 2 shows several exemplary embodiments of configurations for culture bags suitable for use in the bags and methods of the disclosure. Bag 200a has only a single port 230a, providing access to compartment 220a. Bag 200b is in the so-called "serpentine" configuration, in which a longer path length through the system can be provided; ports 230b and 240b are connected by a serpentine path formed by serpentine-shaped compartment 220b formed by appropriate welding of the sheets forming the bag. And bag 200c has a non-rectangular shape, with a corresponding non-rectangular compartment 220c between ports 230c and 240c.

One or more of the walls of the container can be porous, and can, for example, be permeable to gases produced and consumed in a cell culture (e.g., $O_2$, $CO_2$) but impermeable to liquids (e.g., water). This can allow for passive exchange of gases across the container walls with the atmosphere to allow for respiration of cells in the bag.

The containers of the disclosure are desirably formed such that there is substantially no contamination of a fluid within the container. Accordingly, it is desirable for the inner surface of the container to be formed from materials that will not leach organics into the fluid. For example, in certain embodiments as otherwise described herein, an inner surface of the container wall is formed of a polymer (e.g., a fluoropolymer such as fluorinated ethylene propylene) having a total organic carbon (TOC) in water of less than 0.1 mg/cm$^2$ (e.g., less than 0.05 mg/cm$^2$, or less than 0.05 mg/cm$^2$). Such containers are described, e.g., in U.S. Patent Application Publications nos. 2016/0178490 and 2016/0178491, each of which is hereby incorporated herein by reference in its entirety; the person of ordinary skill in the art can, based on the description herein, adapt such containers for use in the containers and methods of the present disclosure. Notably, containers of the disclosure need not have reactive functional groups at the inner surfaces thereof, although in some cases, such as when the degradable carrier is a degradable coating, reactive functional groups can be used to covalently attach the degradable carrier to the inner surface of the container as described below.

The container contains a degradable carrier, and the carrier comprises a plurality of biological agent-capturing moieties. As used herein, a biological agent-capturing moiety is a material with which the biological agent can selectively associate. The association between a biological agent and a respective capturing moiety is sufficient to retain the biological agent on the carrier (e.g., throughout centrifugation or filtration), and may be covalent or non-covalent. In certain embodiments as otherwise described herein, the biological agent-capturing moiety comprises one or more aptamers. In certain such embodiments, the one or more aptamers are selected from peptides, polypeptides, oligonucleotides, and polynucleotides (i.e., DNA and RNA). For example, in certain embodiments as otherwise described herein, the biological agent-capturing moiety comprises an oligonucleotide aptamer selected from a random, synthetically generated sequence pool.

In certain embodiments as otherwise described herein, the biological agent-capturing moiety comprises a DNA aptamer having at least two sites to which the biological agent can selectively associate. For example, in certain such embodiments, at least 5, or at least 10, or at least 25, or at least 50, or at least 75, or at least 100 instances of a nucleotide subsequence selective for the biological agent are present in the DNA aptamer sequence.

In certain embodiments as otherwise described herein, the biological agent-capturing moiety comprises a plurality of aptamers (e.g., oligonucleotide aptamers) attached to a polypeptide. For example, in certain embodiments as otherwise described herein, the biological agent-capturing moiety comprises a plurality of biotinylated aptamers attached to an avidin protein. In certain such embodiments, the biotinylated aptamers comprise oligonucleotides or polypeptides. In certain such embodiments, the biological agent-capturing moiety comprises at least 10, or at least 25, or at least 50, or at least 75, or at least 100, or at least 200, or at least 300, or at least 400, or at least 500, or at least 600, or at least 700, or at least 800, or at least 900, or at least 1000 aptamers (e.g., biotinylated aptamers attached to an avidin protein). In certain such embodiments, the biological agent-capturing moiety comprises a number of aptamers (e.g., biotinylated aptamers attached to an avidin protein) within the range of 10 to 1000, or 10 to 900, or 10 to 800, or 10 to 700, or 10 to 600, or 10 to 500, or 10 to 400, or 10 to 300, or 10 to 200, or 25 to 1000, or 50 to 1000, or 100 to 1000, or 200 to 1000, or 300 to 1000, or 400 to 1000, or 500 to 1000, or 600 to 1000, or 700 to 1000, or 800 to 1000, or 10 to 400, or 100 to 500, or 200 to 600, or 300 to 700, or 400 to 800, or 500 to 900, or 600 to 1000.

In certain embodiments as otherwise described herein, the biological agent is selected from inorganic species and organic small molecules. For example, in certain such embodiments, the biological agent is a metal ion. In other such embodiments, the biological agent is a vitamin, hormone, or peptide. In certain embodiments as otherwise described herein, the biological agent is a macromolecule such as, for example, a protein, an enzyme, or a nucleic acid (i.e., DNA or RNA). In certain embodiments as otherwise described herein, the biological agent is complex biological system such as, for example, a cell organelle (e.g., nucleus, ribosome, mitochondria, vacuole, rough endoplasmic reticulum, smooth endoplasmic reticulum, Golgi apparatus, lysosome, centrosome, vesicle, membrane) or a cell fragment. In certain embodiments as otherwise described herein, the biological agent is a bacterium or a cell group.

In certain embodiments as otherwise described herein, the biological agent is a cell (e.g., a normal cell or a diseased cell). For example, in certain embodiments as otherwise described herein, the cell is a blood cell, a stem cell, or an immune cell. In certain such embodiments, the cell is a white blood cell. In certain such embodiments, the cell is a monocyte. In certain such embodiments, the cell is a stem cell such as, for example, a mesenchymal stem cell, or a progenitor cell. In certain embodiments as otherwise described herein, the cell is a T cell (e.g., a regulatory T cell), an endothelial progenitor cell, or a natural killer cell. The person of ordinary skill in the art will appreciate that the biological agent can, in certain embodiments, be a desirable biological agent, capturable for retention in a cell culture (i.e., positive selection), and can alternatively, in other embodiments, be an undesirable biological agent, capturable for removal from a cell culture (i.e., negative selection).

For example, in certain embodiments as otherwise described herein, the biological agent-capturing moiety comprises one or more aptamers that can selectively associate with the CD31 marker of an endothelial progenitor cell. In another example, in certain embodiments as otherwise described herein, the biological agent-capturing moiety comprises one or more aptamers that can selective associate with one or more markers of a T regulatory cell (e.g., CD4, CD25, CD27). In yet another example, in certain embodiments as otherwise described herein, the biological agent-capturing moiety comprises one or more aptamers that can selectively associate with one or more markers of a mesenchymal stem cell (e.g., CD73, CD90, CD105). In certain such embodiments, the biological agent-capturing moiety comprises a plurality of aptamers (e.g., oligonucleotide aptamers) attached to a polypeptide.

As used herein, a degradable carrier is a material having in an undegraded state a surface to which the biological agent-capturing moieties can be attached (e.g., through a covalent linker). The carrier can remain in an undegraded state in the presence of, for example, an aqueous medium for at least a period of time sufficient to culture or isolate a biological agent, or even indefinitely. The carrier can be degraded into fragments or can be partially or completely dissolved, and in a degraded state can be separated from the biological agent.

In certain embodiments as otherwise described herein, the biological agent-capturing moiety is covalently linked to a functional group of the surface of the degradable carrier. For example, the surface of the degradable carrier may be functionalized with a carboxyl group, hydroxyl group, aldehyde group, carbonyl group, amine group, imine group, amide group, ester group, anhydride group, thiol group, disulfide, phenol, guanidine, thioether, indole, imidazole, or diazonium group. The person of ordinary skill in the art will understand that these "functional groups" are identified as the group to which the biological agent-capturing moiety is covalently linked; e.g., an "amine" functional group can be attached to a carboxy-bearing biological agent-capturing moiety to form a carboxamide bond to the biological agent-capturing moiety.

In certain such embodiments, the biological agent-capturing moiety comprises a plurality of aptamers (e.g., oligonucleotide aptamers) attached to a protein, the protein attached through a peptide linkage to a carboxyl group of the surface of the degradable carrier. In other such embodiments, the biological agent-capturing moiety comprises an amine-terminated aptamer (e.g., a DNA aptamer) attached through an imine linkage to an aldehyde group of the surface of the degradable carrier.

Though the number of biological agent-capturing moieties per unit of degradable carrier surface (i.e., capturing moiety density) is not particularly limited, the person of ordinary skill in the art will appreciate that the capturing moiety density can, typically, be greater than the number of biological agents (e.g., cells) that can be captured per unit of degradable carrier surface (i.e., captured agent density). Accordingly, in certain embodiments, the capturing moiety density of the degradable carrier is greater than the captured agent density of the degradable carrier.

Figure 3:
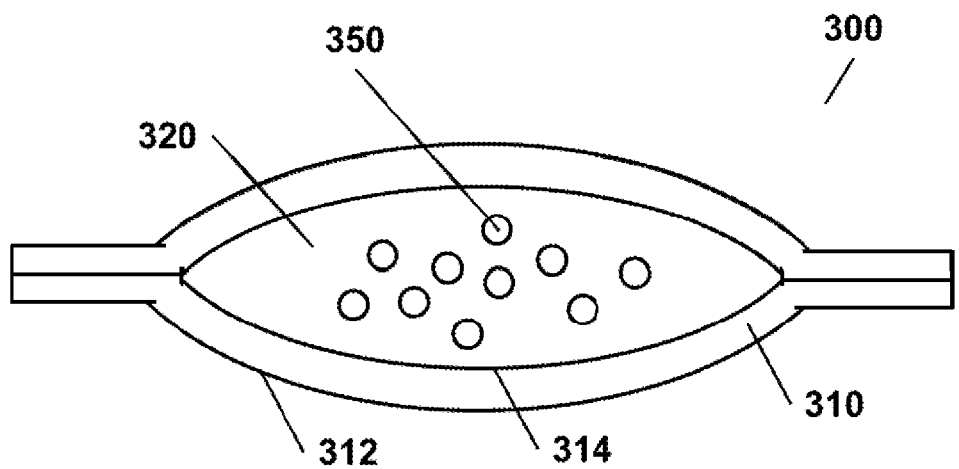
FIG. 3 is a schematic cross-sectional view of a bag according to one embodiment of the disclosure.

In certain embodiments as otherwise described herein, the degradable carrier comprises a plurality of degradable microcarriers (e.g., polymer microcarriers), the microcarriers having a surface to which the biological agent-capturing moieties can be attached. For example, bag 300 of FIG. 3 includes a bag wall 310 (having an outer surface 312 and an inner surface 314) enclosing a compartment 320, compartment 320 containing a plurality of degradable microcarriers 350. In certain embodiments, the average size of the microcarriers is within the range of 0.5 µm to 1000 µm, or 0.5 µm to 900 µm, or 0.5 µm to 800 µm, or 0.5 µm to 700 µm, or 0.5 µm to 600 µm, or 0.5 µm to 500 µm, or 0.5 µm to 400 µm, or 0.5 µm to 300 µm, or 0.5 µm to 250 µm, or 1 µm to 1000 µm, or 5 µm to 1000 µm, or 10 µm to 1000 µm, or 25 µm to 1000 µm, or 50 µm to 1000 µm, or 100 µm to 1000 µm, or 200 µm to 1000 µm, or 300 µm to 1000 µm, or 400 µm to 1000 µm, or 500 µm to 1000 µm, or 10 µm to 750 µm, or 10 µm to 500 µm, or 20 µm to 400 µm, or 50 µm to 300 µm.

Figure 4:
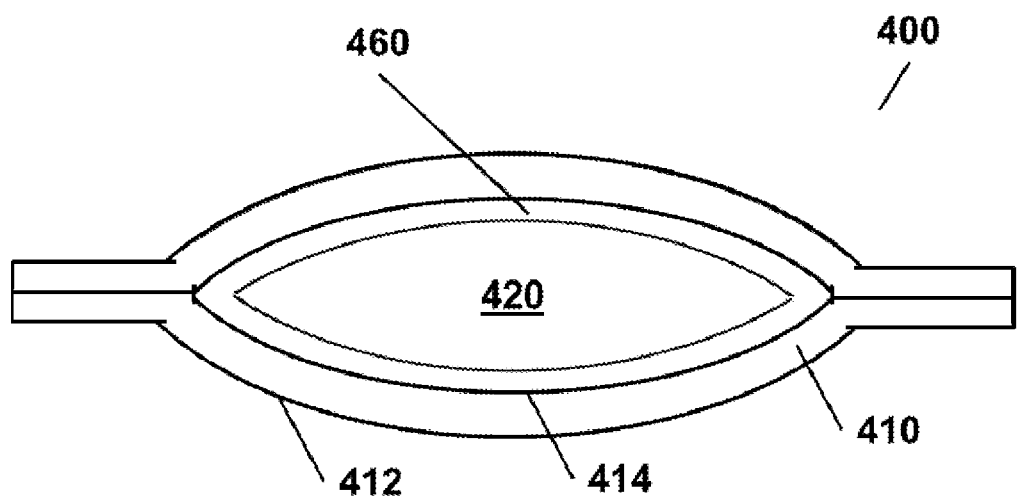
FIG. 4 is a schematic cross-sectional view of a bag according to one embodiment of the disclosure.

In certain embodiments as otherwise described herein, the degradable carrier comprises a degradable coating (e.g., a polymer coating) disposed adjacent to at least a portion (e.g., at least a majority, or even all) of the inner surface of the container. In certain such embodiments, the degradable coating is covalently attached to the inner surface of the container. For example, bag 400 of FIG. 4 includes a bag wall 410 (having an outer surface 412 and an inner surface 414) enclosing a sealed compartment 420, sealed compartment 420 containing a degradable coating 460 disposed adjacent to (e.g., covalently attached to) inner surface 414. In certain such embodiments, the degradable coating has a thickness within the range of 10 nm (e.g., about a monolayer) to 10 mm, or 10 nm to 1 mm, or 10 nm to 500 µm, or 10 nm to 100 µm, or 10 nm 1 µm, or 1 µm to 10 mm, or 100 µm to 10 mm, or 500 µm to 10 mm, or 1 mm to 10 mm. In certain such embodiments, the degradable coating is covalently linked to a functional group of the inner surface of the container (e.g., a functional group of the fluoropolymer comprising the inner surface). In certain embodiments, the functional group is a carboxyl group, hydroxyl group, aldehyde group, carbonyl group, amine group, imine group, amide group, ester group, anhydride group, thiol group, disulfide, phenol, guanidine, thioether, indole, imidazole, or diazonium group.

In certain embodiments as otherwise described herein, the degradable carrier comprises a cleavable polymer. For example, in certain such embodiments, the degradable carrier comprises an enzyme-cleavable polymer such as, for example, a polysaccharide. In certain such embodiments, the polysaccharide is a starch (e.g., cleavable by alpha-amylase). In other such embodiments, the polysaccharide is a polygalacturonic acid (e.g., cleavable by pectinase). In another example, in certain such embodiments, the degradable carrier comprises a hydrolyzable polymer such as, for example, poly(lactic-co-glycolic acid) (PLGA), polylactic acid (PLA), or polycaprolactone. In certain such embodiments, the polymer hydrolysis is accelerated at a pH below 6, or at a pH above 8. In certain such embodiments, the polymer hydrolysis is accelerated in the presence of a hydrolysis catalyst such as, for example, an amine.

In certain embodiments as otherwise described herein, the degradable carrier comprises a cross-linked polymer having, for example, a number of cross-links sufficient to provide a carrier that can remain undegraded in an aqueous medium. In certain such embodiments, the degradable carrier comprises an enzyme-cleavable polymer (e.g., a polysaccharide)

having a number of cross-links (e.g., glycerol diether cross-links) sufficient to provide a carrier that can remain undegraded in an aqueous medium having less than a critical level of the enzyme. In other such embodiments, the degradable carrier comprises a hydrolyzable polymer (e.g., PLGA, PLA, or polycaprolactone) having a number of cross-links sufficient to provide a carrier that can remain undegraded in an aqueous medium having less than a critical level of a hydrolysis catalyst, or in an aqueous medium having a pH outside of a critical range. In another example, in certain embodiments as otherwise described herein, the degradable carrier comprises an insoluble cross-linked network of an otherwise soluble polymer. For example, in certain such embodiments, a degradable carrier comprising a thioether-cross-linked polymer network (e.g., a hydrogel) can remain undegraded in an aqueous medium having less than a critical level of glutathione.

In certain embodiments, a cross-linked polymer of the degradable carrier comprises a cross-linker that prevents enzyme cleavage of the polymer (e.g., of a polysaccharide). For example, in certain such embodiments, a degradable carrier comprising a $Ca^{2+}$-cross-linked polysaccharide (e.g., polygalacturonic acid) can remain undegraded in an aqueous medium having less than a critical level of a $Ca^{2+}$-chelating agent (e.g., EDTA), i.e., even if the medium includes more than a critical level of a cleaving enzyme (e.g., pectinase).

In certain embodiments as otherwise described herein, the degradable carrier is degradable upon, or the degradation of the degradable carrier is accelerated upon, irradiation (e.g., with radiation having a wavelength of less than 450 nm, or less than 420 nm). In certain embodiments as otherwise described herein, the degradable carrier is degradable upon, or the degradation of the degradable carrier is accelerated upon, exposure to an elevated temperature (e.g., greater than 37° C., or greater than 40° C.).

In certain embodiments as otherwise described herein, the inner surface of the container comprises a fluoropolymer selected from polytetrafluoroethylene (PTFE), perfluoroalkoxy (PFA), ethylene tetrafluoroethylene (ETFE), polyvinylidene fluoride (PVDF), polychlorotrifluoroethylene (PCTFE), ethylene chlorotrifluoroethylene (ECTFE), fluorinated ethylene propylene (FEP), ethylene fluorinated ethylene propylene (EFEP), perfluoropolyether (PFPE), modified polytetrafluoroethylene (TFM), polyvinyl fluoride (PVF), or any mixture thereof. For example, in certain embodiments as otherwise described herein, the inner surface of the container comprises fluorinated ethylene propylene. In certain embodiments as otherwise described herein, the inner surface of the container consists essentially of, or is the fluoropolymer (e.g., fluorinated ethylene propylene). In certain embodiments as otherwise described herein, the material comprising the inner surface of the bag has a thickness of at least 0.0003 inches, at least 0.0004 inches, at least 0.0005 inches, at least 0.0006 inches, at least 0.001 inches, or at least 0.10 inches. For example, in certain such embodiments, the material at the inner surface of the container has a thickness within the range of 0.0003 inches to 0.2 inches, or 0.0003 inches to 0.1 inches, or 0.0005 inches to 0.08 inches, or 0.001 inches to 0.07 inches, or 0.001 inches to 0.05 inches, or 0.001 inches to 0.03 inches, or 0.001 inches to 0.018 inches, or 0.001 inches to 0.016 inches, or 0.001 inches to 0.014 inches, or 0.001 inches to 0.012 inches.

In certain embodiments as otherwise described herein, the material making up the container wall is a multilayer material, with a layer of fluoropolymer at the inner surface thereof, and a layer of another polymeric material (fluoropolymeric or otherwise) at the outer surface thereof. In certain embodiments as otherwise described herein, the material at the outer surface of the container has a thickness of at least 0.0005 inches, or at least 0.001 inches, or at least 0.005 inches, or at least 0.0075 inches, or at least 0.01 inches, or at least 0.02 inches, or at least 0.03 inches, or at least 0.04 inches, or at least 0.05 inches, or at least 0.06 inches, or at least 0.07 inches, or at least 0.08 inches, or at least 0.09 inches, or at least 0.1 inches, or at least 0.11 inches. For example, in certain such embodiments, the material at the outer surface of the container has a thickness within the range of 0.0005 inches to 0.2 inches, or 0.005 inches to 0.18 inches, or 0.01 inches to 0.16 inches, or 0.01 inches to 0.14 inches, or 0.01 inches to 0.12 inches, or 0.06 inches to 0.13 inches, or 0.09 inches to 0.126 inches.

In certain embodiments, the degradable carrier comprises a plurality of microcarriers and the inner surface of the container further comprises a plurality of biological agent-capturing moieties as described herein. In certain embodiments as otherwise described herein, the biological agent-capturing moieties attached to the inner surface of the container are the same as the biological agent-capturing moieties of the degradable carrier. In other embodiments, the biological agent-capturing moieties attached to the inner surface of the container are selective for a biological agent other than the agent for which the biological agent-capturing moieties of the degradable carrier are selective. Advantageously, the present inventors have determined that such containers can improve biological agent capture efficiency, or can facilitate the isolation and separation of two distinct biological agents.

In certain embodiments as otherwise described herein, the outer surface of the container comprises a material other than a fluoropolymer. For example, in certain such embodiments, the material of the outer surface of the container comprises a thermoplastic polymer, a thermoplastic elastomer, a silicon, a rubber, or any combination thereof. Alternatively, the outer surface of the container can, in certain embodiments as otherwise described herein, comprise a fluoropolymer such as, for example, the fluoropolymer of the inner surface. In certain such embodiments, the material of the inner surface and the outer surface (i.e., the container wall) consists essentially of, or is the fluoropolymer (e.g., fluorinated ethylene propylene).

In certain embodiments as otherwise described herein, the container includes the biological agent. In certain such embodiments, the biological agent is attached to the carrier through the biological agent-capturing moiety. For example, in certain such embodiments, the biological agent is a cell associated with the carrier through an aptamer bound to the surface of a degradable microcarrier, or a degradable coating. In certain embodiments, the inner surface of the container comprises a plurality of the biological agent-capturing moieties, at least a portion of which are attached to the biological agent. For example, in certain such embodiments, the biological agent is a cell, and can associate with an aptamer bound to the surface of a degradable microcarrier, or with an aptamer bound to the inner surface of the container. In certain such embodiments, the biological agent-capturing moiety of the degradable microcarriers is the same as the biological agent-capturing moiety at the inner surface of the container.

In certain embodiments as otherwise described herein, the container further includes an aqueous medium. The aqueous medium can be, for example, a cell culture medium comprising a biological agent and one or more off-target agents. As used herein, off-target agents are materials other than the biological agent (i.e., capturable by the biological agent-capturing moiety) including, for example, cells other than the biological agent, cell fragments, proteins, vitamins, hormones, peptides, and metal ions.

In certain embodiments as otherwise described herein, the container includes an off-target agent (e.g., a cell other than the biological agent), and no more than 20% of the off-target agent is adhered to the degradable carrier or the inner surface of the container. For example, in certain such embodiments less than 17.5%, or less than 15%, or less than 12.5%, or less than 10%, or less than 7.5%, or less than 5%, or less than 4%, or less than 3%, or less than 2%, or less than 1% of the off-target agent is adhered to the degradable carrier or the inner surface of the container.

Another aspect of the disclosure is a cell isolation system including a container as otherwise described herein. For example, in certain embodiments as otherwise described herein, the cell isolation system comprises a container as otherwise described herein containing an aqueous medium, and a rocker configured to mix the aqueous medium and the carrier. In another example, in certain embodiments as otherwise described herein, the cell isolation system comprises a container as otherwise described herein containing an aqueous medium, and a centrifuge configured to separate the carrier (e.g., comprising a plurality of degradable microcarriers) from the aqueous medium. In yet another example, in certain embodiments as otherwise described herein, the cell isolation system comprises a container as otherwise described herein containing an aqueous medium, and a filter in fluid communication with an outlet of the container configured to separate the carrier (e.g., comprising a plurality of degradable microcarriers) from the aqueous medium. In certain embodiments, the aqueous medium in the container of the cell isolation system includes an off-target agent such as, for example, a cell other than the biological agent.

Advantageously, the present inventors have determined that degradation of the carrier described herein can release a captured (e.g., and isolated) biological agent into aqueous medium (e.g., to be stored or further cultured) without deleteriously affecting cell function. Desirably, the fluoropolymer of the inner surface can prevent adhesion of materials other than the biological agent (i.e., off-target agents), increasing the purity of a biological agent isolated in the container.

Accordingly, another aspect of the disclosure is a method for cultivating a biological agent, the method including providing a container as otherwise described herein containing the biological agent, and mixing the biological agent and the carrier in a first aqueous medium contained in the container. The method further includes removing the first aqueous medium from the container, adding a second aqueous medium to the container, and degrading the carrier.

In certain embodiments as otherwise described herein, the container contains a blood sample (e.g., a whole blood sample) including the biological agent. For example, in certain such embodiments, the container contains a blood sample and the biological agent is a monocyte. In certain embodiments, the container further includes one or more off-target agents. For example, in certain such embodiments, the container contains a sample (e.g., a whole blood sample) including the biological agent (e.g., a monocyte, a stem cell, a T cell, an endothelial progenitor cell, or a natural killer cell) and one or more off-target agents (e.g., a cell other than the biological agent).

In certain embodiments as otherwise described herein, the first aqueous medium is a cell culture medium. In certain such embodiments, the biological agent is a cell, and the biological agent is cultured in the container (i.e., the agent is grown, or expanded, in the first aqueous medium). Of course, one or more off-target agents comprising the aqueous medium (e.g., included in a whole blood sample contained in the container) may also expand in the first aqueous medium. In certain embodiments as otherwise described herein, the biological agent and carrier are mixed on a rocker. The mixing is performed for a period of time sufficient to allow the biological agent-capturing moiety and the biological agent to associate. In certain embodiments as otherwise described herein, the biological agent is a cell, and the mixing is performed for a period of time and at a temperature sufficient to expand the biological agent. In certain embodiments, the mixing is performed on a rocker.

In certain embodiments as otherwise described herein, the carrier comprises a plurality of degradable microcarriers, and removing the first aqueous medium comprises sedimenting the carriers and decanting the first aqueous medium from the container. For example, in certain such embodiments, removing the first aqueous medium comprises sedimenting the microcarriers with a centrifuge and decanting the first aqueous medium from the container. In certain embodiments as otherwise described herein, the first aqueous medium is removed from the container through a filter configured to retain the microcarriers. For example, in certain such embodiments, the first aqueous medium is removed from the container through a filter having a pore size smaller than the degradable microcarriers in an undegraded state.

In other embodiments, the carrier comprises a degradable coating disposed adjacent the inner surface of the container, and removing the first aqueous medium comprises decanting the first aqueous medium from the container (i.e., without sedimentation or filtration).

Of course, the person of ordinary skill in the art will appreciate that a minor amount of the first aqueous medium can be retained in the container.

Following removal of the first aqueous medium, the container as otherwise described herein can contain cells including, for example, the biological agent and optionally one or more off-target agents. Desirably, a majority of the cells remaining in the container can comprise the biological agent attached to the degradable carrier and optionally to the inner surface of the container through the biological agent-capturing moiety. For example, in certain embodiments as otherwise described herein, the biological agent is a cell, and at least 80%, or at least 82.5%, or at least 85%, or at least 87.5%, or at least 90%, or at least 92.5%, or at least 95%, or at least 97.5%, or at least 98%, or about 98.5%, or at least 99% of the cells in the container after removing the first aqueous medium are the biological agent.

In certain embodiments as otherwise described herein, degrading the carrier comprises subjecting the carrier to a pH different than the pH of the first aqueous medium. For example, in certain embodiments as otherwise described herein, degrading the carrier comprises subjecting the carrier to a pH below 6 or above 8. In certain such embodiments, the second aqueous medium added to the container has a pH below 6 or above 8. In other such embodiments, the pH of the second aqueous medium is adjusted after adding the second aqueous medium to the container. In certain embodiments as otherwise described herein, degrading the carrier comprises contacting the carrier with a hydrolysis catalyst (e.g., an amine catalyst). In certain such embodiments, the second aqueous medium added to the container contains a hydrolysis catalyst. In other such embodiments, a hydrolysis catalyst is added to the container after adding the second aqueous medium. In certain embodiments, the pH of the second aqueous medium enables, or even accelerates the hydrolysis reaction catalyzed by the hydrolysis catalyst. In certain embodiments as otherwise described herein, degrading the carrier comprises contacting the carrier with an enzyme, or an enzyme and a chelating agent. In certain such embodiments, the second aqueous medium added to the container contains an enzyme. In other such embodiments, an enzyme is added to the container after adding the second aqueous medium. In certain embodiments as otherwise described herein, degrading the carrier comprises subjecting the carrier to an elevated temperature (e.g., a temperature greater than 37° C., or greater than 40° C.). In certain embodiments as otherwise described herein, degrading the carrier comprises irradiating the carrier (e.g., with radiation having a wavelength of less than 450 nm, or less than 420 nm).

Advantageously, the present inventors have determined that degrading (e.g., fragmenting, partially dissolving, or dissolving) the carrier can separate a captured biological agent from the carrier without deleteriously affecting the biological agent. In certain embodiments as otherwise described herein, the method further comprises culturing the biological agent in the second aqueous medium (i.e., including the degraded carrier). In certain such embodiments, the second aqueous medium is a cell culture medium. In certain embodiments as otherwise described herein, the method further comprises removing the degraded carrier, for example by sedimenting the biological agent and removing the second aqueous medium, and adding a third aqueous medium to the container. In certain such embodiments, the third aqueous medium is a cell culture medium, or a cell storage medium.

Additional aspects of the disclosure are provided by the enumerated embodiments listed below, which can be combined in any number and in any fashion that is not technically or logically inconsistent.

Embodiment 1

A container (e.g., in the form of a bag) having an outer surface and an inner surface, the inner surface comprising a fluoropolymer, and contained in the container, a degradable carrier;
wherein the carrier comprises a plurality of biological agent-capturing moieties.

Embodiment 2

The container of embodiment 1, wherein the degradable carrier comprises a plurality of degradable microcarriers, each microcarrier comprising a plurality of biological agent-capturing moieties.

Embodiment 3

The container of embodiment 2, wherein the average diameter of the microcarriers is within the range of about 0.5 µm to about 1000 µm (e.g., about 5 µm to about 750 µm, or about 10 µm to about 500 µm, or about 25 µm to about 300 µm).

Embodiment 4

The container of embodiments 2 or 3, wherein the inner surface of the container comprises a plurality of biological agent-capturing moieties.

Embodiment 5

The container of embodiment 1, wherein the degradable carrier comprises a degradable coating disposed adjacent to at least a portion (e.g., at least a majority) of the inner surface of the container.

Embodiment 6

The container of any of embodiments 1-5, wherein the biological agent-capturing moiety comprises one or more aptamers.

Embodiment 7

The container of any of embodiments 1-6, wherein the biological agent is a cell.

Embodiment 8

The container of embodiment 7, wherein the cell is a blood cell or an immune cell.

Embodiment 9

The container of embodiment 7, wherein the cell is a monocyte, a stem or progenitor cell (e.g., a mesenchymal stem cell), a T cell (e.g., a regulatory T cell), an endothelial progenitor cell, or a natural killer cell.

Embodiment 10

The container of any of embodiments 1-9, wherein the degradable carrier comprises a polymer.

Embodiment 11

The container of embodiment 10, wherein the degradable carrier comprises a polysaccharide (e.g., starch or polygalacturonic acid).

Embodiment 12

The container of embodiment 10, wherein the degradable carrier comprises one or more polymers selected from poly(lactic-co-glycolic acid) (PLGA), polylactic acid (PLA), and polycaprolactone.

Embodiment 13

The container of any of embodiments 10-12, wherein the polymer is crosslinked (e.g., thioether cross-linked, $Ca^{2+}$ cross-linked, or glycerol diether cross-linked).

Embodiment 14

The container of any of embodiments 1-13, wherein the carrier is degradable in water at a pH below 6, or at a pH above 8.

Embodiment 15

The container of any of embodiments 1-13, wherein the carrier is degradable in water upon contact with a hydrolysis catalyst (e.g., an amine catalyst).

Embodiment 16

The container of any of embodiments 1-13, wherein the carrier is degradable in water upon contact with an enzyme, or an enzyme and a chelating agent.

Embodiment 17

The container of embodiment 16, wherein the enzyme is an amylase or a pectinase.

Embodiment 18

The container of any of embodiments 1-13, wherein the carrier is degradable in water upon exposure to an elevated temperature (e.g., a temperature greater than 37° C., or greater than 40° C.).

Embodiment 19

The container of any of embodiments 1-13, wherein the carrier is degradable in water upon irradiation (e.g., with radiation having a wavelength of less than 450 nm, or less than 420 nm).

Embodiment 20

The container of any of embodiments 1-19, wherein the fluoropolymer is polytetrafluoroethylene (PTFE), perfluoroalkoxy (PFA), ethylene tetrafluoroethylene (ETFE), polyvinylidene fluoride (PVDF), polychlorotrifluoroethylene (PCTFE), ethylene chlorotrifluoroethylene (ECTFE), fluorinated ethylene propylene (FEP), ethylene fluorinated ethylene propylene (EFEP), perfluoropolyether (PFPE), modified polytetrafluoroethylene (TFM), polyvinyl fluoride (PVF), or any mixture thereof.

Embodiment 21

The container of any of embodiments 1-19, wherein the fluoropolymer is fluorinated ethylene propylene (FEP).

Embodiment 22

The container of any of embodiments 1-21, wherein the degradable carrier is attached to the biological agent, the biological agent attached to the carrier through the biological agent-capturing moiety.

Embodiment 23

The container of any of embodiments 1-22, containing an aqueous medium.

Embodiment 24

The container of embodiment 23, containing an off-target agent.

Embodiment 25

The container of embodiment 24, wherein the off-target agent is a cell other than the biological agent.

Embodiment 26

The container of embodiment 24 or 25, wherein less than 20% (e.g., less than 15%, less than 10%, less than 5%, or less than 1%) of the off-target agent is adhered to the carrier or the inner surface of the container.

Embodiment 27

A cell isolation system comprising the container of any of embodiments 23-25 and a rocker configured to mix the carrier and the aqueous medium.

Embodiment 28

A cell isolation system comprising the container of any of embodiments 23-25 and a centrifuge configured to separate the carrier from the aqueous medium.

Embodiment 29

A cell isolation system comprising the container of any of embodiments 23-25 and a filter in fluid communication with an outlet of the container, the filter configured to separate the carrier from the aqueous medium.

Embodiment 30

A method for cultivating a biological agent, comprising
providing a container according to any of embodiments 1-21, the container containing the biological agent;
mixing the biological agent and the carrier in a first aqueous medium contained in the container;
removing the first aqueous medium from the container;
adding a second aqueous medium to the container; and
degrading the carrier.

Embodiment 31

The method of embodiment 30, wherein the carrier comprises a plurality of degradable microcarriers, and wherein removing the first aqueous medium comprises sedimenting the microcarriers with a centrifuge and decanting the first aqueous medium from the container.

Embodiment 32

The method of embodiment 30, wherein the carrier comprises a plurality of degradable microcarriers, and wherein the first aqueous medium is removed from the container through a filter configured to retain the microcarriers.

Embodiment 33

The method of embodiment 30, wherein the carrier comprises a degradable coating disposed adjacent the inner surface of the container, and wherein removing the first aqueous medium comprises decanting the first aqueous medium from the container.

Embodiment 34

The method of any of embodiments 30-34, wherein
the biological agent is a cell; and at least 80% (e.g., at least 85%, or at least 90%, or at least 95%, or at least 98%, or at least 99%) of the cells in the container after removing the first aqueous medium are the biological agent.

Embodiment 35

The method of any of embodiments 30-34, wherein degrading the carrier comprises subjecting the carrier to a pH below 6 or about 8.

Embodiment 36

The method of any of embodiments 30-34, wherein degrading the carrier comprises contacting the carrier with a hydrolysis catalyst (e.g., an amine catalyst).

Embodiment 37

The method of any of embodiments 30-34, wherein degrading the carrier comprises contacting the carrier with an enzyme and, optionally, a chelating agent.

Embodiment 38

The method of any of embodiments 30-34, wherein degrading the carrier comprises exposing the carriers to an elevated temperature (e.g., a temperature greater than 37° C., or greater than 40° C.).

Embodiment 39

The method of any of embodiments 30-34, wherein degrading the carrier comprises irradiating the carriers (e.g., with radiation having a wavelength of less than 450 nm, or less than 420 nm).

Embodiment 40

The method of any of embodiments 30-39, further comprising removing the degraded carriers from the container.

Embodiment 41

The container or method of any of claims 1-40, wherein the container is in the form of a bag.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, with a precision that is typical in the art.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Numerous references have been made to patents and printed publications throughout this specification. Each of the cited references and printed publications are individually incorporated herein by reference in their entirety.

Furthermore, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A cell culture system comprising:
   a container having an outer surface and an inner surface, the inner surface comprising a fluoropolymer;
   a first aqueous medium contained in the container; and
   a plurality of degradable microcarriers contained in the container, each of the degradable microcarriers comprising
      a body formed of a hydrolyzable polymer, the body having a surface, and
      a plurality of cell-capturing moieties attached to the surface of the body, each of the cell-capturing moieties being capable of selectively associating with a cell of a first type.

2. The cell culture system of claim 1, wherein the degradable microcarriers have an average diameter in the range of 0.5 µm to 1000 µm.

3. The cell culture system of claim 1, wherein each of the plurality of the cell-capturing moieties comprises one or more nucleotide aptamers.

4. The cell culture system of claim 1, wherein the cell is a blood cell or an immune cell.

5. The cell culture system of claim 1, wherein the hydrolyzable polymer comprises a polysaccharide.

6. The cell culture system of claim 1, wherein the hydrolyzable polymer comprises one or more polymers selected from poly(lactic-co-glycolic acid) (PLGA), polylactic acid (PLA), and polycaprolactone.

7. The cell culture system of claim 1, the degradable microcarriers are degradable in water at a pH below 6, or at a pH above 8.

8. The cell culture system of claim 1, wherein the degradable microcarriers are degradable in water upon contact with a hydrolysis catalyst.

9. The cell culture system of claim 1, wherein the degradable microcarriers are degradable in water upon contact with an enzyme, or an enzyme and a chelating agent.

10. The cell culture system of claim 1, wherein the degradable microcarriers are degradable in water upon exposure to a temperature greater than 40° C.

11. The cell culture system of claim 1, wherein the degradable microcarriers are degradable in water upon irradiation.

12. The cell culture system of claim 1, wherein the fluoropolymer is polytetrafluoroethylene (PTFE), perfluoroalkoxy (PFA), ethylene tetrafluoroethylene (ETFE), polyvinylidene fluoride (PVDF), polychlorotrifluoroethylene (PCTFE), ethylene chlorotrifluoroethylene (ECTFE), fluorinated ethylene propylene (FEP), ethylene fluorinated ethylene propylene (EFEP), perfluoropolyether (PFPE), modified polytetrafluoroethylene (TFM), polyvinyl fluoride (PVF), or any mixture thereof.

13. The cell culture system of claim 1, further comprising a first plurality of cells of the first type contained in the container, wherein each of the first plurality of cells of the first type is attached to a degradable microcarrier of the plurality of degradable microcarriers through a biological agent-capturing moiety thereof.

14. The cell culture system of claim 1, further comprising an off-target agent contained in the container, wherein the off-target agent is a a second plurality of cells of a second type other than the first type, wherein less than 20% of the off-target agent is attached to the degradable carrier.

15. The cell culture system of claim 1 further comprising one or more of a rocker configured to mix the plurality of degradable microcarriers and the first aqueous medium, a centrifuge configured to separate the plurality of degradable microcarriers from the first aqueous medium, and a filter in fluid communication with an outlet of the container and configured to separate the plurality of degradable microcarriers from the first aqueous medium.

16. The cell culture system of claim 1, wherein
   each of the plurality of the cell-capturing moieties comprises one or more aptamers;
   the hydrolyzable polymer comprises one or more polymers selected from poly(lactic-co-glycolic acid) (PLGA), polylactic acid (PLA), and polycaprolactone;
   the fluoropolymer is polytetrafluoroethylene (PTFE), perfluoroalkoxy (PFA), ethylene tetrafluoroethylene (ETFE), polyvinylidene fluoride (PVDF), polychlorotrifluoroethylene (PCTFE), ethylene chlorotrifluoroethylene (ECTFE), fluorinated ethylene propylene (FEP), ethylene fluorinated ethylene propylene (EFEP), perfluoropolyether (PFPE), modified polytetrafluoroethylene (TFM), polyvinyl fluoride (PVF), or any mixture thereof, the cell culture system further comprising a first plurality of cells of the first type contained in the container, wherein each of the first plurality of cells of the first type is attached to a degradable microcarrier of the plurality of degradable microcarriers through a biological agent-capturing moiety thereof.

17. The cell culture system of claim 16, further comprising an off-target agent contained in the container, wherein the off-target agent is a second plurality of cells of a second type other than the first type, wherein less than 20% of the off-target agent is attached to the degradable carrier.

18. A method for cell cultivation, comprising providing a cell culture system according to claim 1;
mixing a first plurality of cells of the first type with the plurality of degradable microcarriers in the first aqueous medium contained in the container;
removing the first aqueous medium from the container; then
adding a second aqueous medium to the container; and
degrading the plurality of degradable microcarriers.

19. The method of claim 18, wherein removing the first aqueous medium comprises sedimenting the degradable microcarriers with a centrifuge and decanting the first aqueous medium from the container; or removing the first aqueous medium from the container through a filter configured to retain the degradable microcarriers.

20. The method of claim 18, wherein at least 80% of cells in the container after removing the first aqueous medium are cells of the first type.

21. The method of claim 18, wherein degrading the plurality of degradable microcarriers comprises subjecting the degradable microcarriers to a pH below 6 or about 8; contacting the degradable microcarriers with a hydrolysis catalyst; contacting the plurality of degradable microcarriers with an enzyme and, optionally, a chelating agent; exposing the plurality of degradable microcarriers to an elevated temperature; or irradiating the plurality of degradable microcarriers.

22. A cell culture system comprising:
a container having an outer surface and an inner surface, the inner surface comprising a fluoropolymer;
a degradable carrier disposed as a coating on the inner surface of the container, the coating comprising
a body formed of a hydrolyzable polymer, the body having a surface, and
a plurality of cell-capturing moieties attached to the surface of the body, each of the cell-capturing moieties being capable of selectively associating with a cell of a first type; and
an aqueous medium contained in the container.

23. The cell culture system of claim 22, wherein the hydrolyzable polymer comprises a polysaccharide.

24. The cell culture system of claim 22, wherein the hydrolyzable polymer comprises one or more polymers selected from poly(lactic-co-glycolic acid) (PLGA), polylactic acid (PLA), and polycaprolactone.

25. The cell culture system of claim 22, further comprising
a first plurality of cells of the first type contained in the container, wherein each of the first plurality of cells of the first type is attached the degradable carrier through a biological agent-capturing moiety thereof, and
an off-target agent contained in the container, wherein the off-target agent is a second plurality of cells of a second type other than the first type, wherein less than 20% of the off-target agent is attached to the degradable carrier.

* * * * *